(12) United States Patent
Ederer et al.

(10) Patent No.: US 8,569,439 B2
(45) Date of Patent: Oct. 29, 2013

(54) HARDENER FOR SILICONE RUBBER MATERIALS

(75) Inventors: Theodor Ederer, Zangberg (DE); Thomas Knott, Mühldorf a. Inn (DE); Ulrich Pichl, Aschau a. Inn (DE); Gerhard Schmidt, Mühldorf a. Inn (DE); Ludwig Waldmann, Mühldorf a. Inn (DE)

(73) Assignee: Nitro-Chemie Aschau GmbH (DE)

( * ) Notice: Subject to any disclaimer, the term of this patent is extended or adjusted under 35 U.S.C. 154(b) by 66 days.

(21) Appl. No.: 12/673,080

(22) PCT Filed: Aug. 29, 2008

(86) PCT No.: PCT/EP2008/007106
§ 371 (c)(1), (2), (4) Date: Aug. 18, 2010

(87) PCT Pub. No.: WO2009/027103
PCT Pub. Date: Mar. 5, 2009

(65) Prior Publication Data
US 2012/0016072 A1    Jan. 19, 2012

(30) Foreign Application Priority Data
Aug. 31, 2007 (EP) .................................... 07017077

(51) Int. Cl.
*C08G 77/04*    (2006.01)

(52) U.S. Cl.
USPC ................... 528/34; 252/182.14; 252/182.18; 556/437; 556/471; 556/470; 556/483

(58) Field of Classification Search
USPC .................... 556/437, 471, 470, 483; 528/34; 252/182.14, 182.18
See application file for complete search history.

(56) References Cited

U.S. PATENT DOCUMENTS 4,552,942 A * 11/1985 Kreuzer et al. ................. 528/34

FOREIGN PATENT DOCUMENTS

EP    0089618    3/1983
JP    58185594   10/1983

OTHER PUBLICATIONS

Article, "Some a-Carbalkoxyalkoxysilanes", dated Apr. 1958, XP 002461949 5 pages.
Sprung, M. M. "Some α-Carbalkoxyalkoxysilanes." The Journal of Organic Chemistry, vol. 23, pp. 1530-1534 (Apr. 15, 1958).
Japanese Office Action mailed May 8, 2012 with partial translation; Japanese Application No. 2010-522255; 3 pages.

* cited by examiner

*Primary Examiner* — Margaret Moore
(74) *Attorney, Agent, or Firm* — Thomas & Karceski, P.C.

(57) ABSTRACT

A hardener for silicone rubber materials comprising a silane compound which comprises a 2-hydroxy-propionic acid alkyl ester radical.

15 Claims, No Drawings

HARDENER FOR SILICONE RUBBER MATERIALS

CROSS-REFERENCE TO RELATED APPLICATION(S)

This is a National Stage Entry into the United States Patent and Trademark Office from International PCT Patent Application No. PCT/EP2008/007106, having an international filing date of 29 Aug. 2008, which relies for priority on European Patent Application No. EP 07017077.4, filed on 31 Aug. 2007, the contents of both of which are incorporated herein by reference.

FIELD OF THE INVENTION

The present invention concerns a hardener for rubber materials. More specifically, the present invention concerns a hardener for silicone rubber materials.

BACKGROUND OF THE INVENTION

Cold-curing silicone rubber materials, also referred to as "RTV" ("Raumtemperaturvernetzende"=cross-linking at room temperature) silicone rubber materials, have been known for quite some time as custom-designed materials which have elastic properties. They are used, generally, as sealants or adhesives for glass, porcelain, ceramics, stone, plastics, metals, wood, etc., in applications like joint filling and sealing compounds in construction and sanitary installations, or as coating agents, e.g. in the electronics industry (Römpp Chemie Lexikon, CD ROM, version 2.0, ed. J. Falbe, Thieme-Verlag, Stuttgart 1999; and Ullmanns Enzyklopädie der Technischen Chemie, 4th edition, ed. E. Bartholome, Verlag Chemie, Weinheim 1982, vol. 21, p. 511 et seq.). Use is made especially of single-component RTV silicone rubber materials (RTV-1), for example, plastically mouldable mixtures made of $\alpha,\omega$-dihydroxy-polyorganosiloxanes and appropriate so-called hardeners, or cross-linking agents, respectively, which are suitable for storing under exclusion of moisture but polymerize under the influence of water or humidity of the air at room temperature.

Preferably, various polyfunctional hardeners, e.g. tri- and/or tetrafunctional hardeners, are used together with various polyorganosiloxanes which either are difunctional or carry more functional groups, depending on the desired polymerization rate as well as the desired chemical and physical properties of the polymerization product, e.g. the desired degree of cross-linking, solvent resistance, etc. The most frequently chosen difunctional polyorganosiloxanes are $\alpha,\omega$-dihydroxy-polyorganosiloxanes. Polymerization, as a rule, takes place by condensation of the SiOH groups which are formed as intermediates by the hydrolysis of suitable hydrolyzable SiX groups of the hardeners. Based on the leaving groups (HX) released by the hydrolysis, a distinction is made with RTV-1 silicone rubber materials between acid systems (HX=acids, e.g. acetic acid), basic systems (e.g. HX=amines), and neutral systems (e.g. HX=alcohol or oxime). Since, when cross-linking, both acid and basic RTV-1 rubber materials release aggressive compounds which have the potential, for example, of corroding or decomposing metal, stone, or mortar, modern RTV-1 silicone rubber materials often are prepared with neutral cross-linking systems. Use is made, for example, of neutral cross-linking alkoxysilane hardeners which are based on methanol and ethanol as leaving groups. Commercially available alkoxy systems, however, are problematic as regards their storage stability and adherence of the polymerized rubber materials. That is why oximosilane hardeners are increasingly used which hydrolyze with release of an alkanone oxime. Especially hardeners which hydrolyze with release of butan-2-one oxime (or methyl-ethyl-ketoxime, MEKO, respectively) are often used at present.

Yet butan-2-one oxime may cause cancer, as has been discovered recently. Therefore, any further use of compounds releasing butan-2-one oxime, on principle, forbids itself for health reasons. That is why, since 2004, butan-2-one oxime must be labelled by the R phrase (risk phrase) "R40" ("suspected of having cancerogenic effects"). As a consequence, also silicone rubber materials must be thus labelled if they contain free butan-2-one oxime in a concentration above a certain threshold. The labelling requirement particularly includes silicone rubber materials like, for example, the ones contained in sealant cartridges, unless the free content of butan-2-one oxime is less than 1% (cf. "mixing rule" of the preparation directive, Directive 2006/8/EG of the Commission of Jan. 23, 2006, published in the Official Journal of the European Union of Jan. 24, 2006).

Practically all of the hardeners mentioned above suffer from another disadvantage, also under health aspects, namely that the compounds released during cross-linking smell awful, sometimes extremely awful, which causes great discomfort, especially, when working with them in closed spaces.

It is important for the formulation of the silicone rubber material that the hardener is liquid at room temperature, and preferably even at distinctly lower temperatures so that its handling will be easy and reliable and it will mix homogenously with the silicone rubber mass proper or the starting materials thereof, respectively. If the liquid state of the hardener is maintained even after transportation at minus temperatures during the winter that saves expenditure in terms of time and energy for melting it at the time of formulation.

Moreover, the hardener should accomplish the most complete polymerization possible of the rubber material in order to avoid subsequent "bleeding" of incompletely reacted starting substances etc. Finally, the polymerization product should be transparent and clear, respectively, when the curing is completed.

SUMMARY OF THE INVENTION

It is, therefore, an object of the invention to provide an improved hardener for silicone rubber materials by which the known disadvantages in the art are eliminated or, at any rate, reduced.

The object of the invention is met by the subject matter of the independent claims. Preferred embodiments are the subject matter of the dependent claims.

DESCRIPTION OF THE DRAWINGS

There are no separate drawings appended to the present patent application. Accordingly, embodiment(s) of the present invention is(are) described without reference to drawings appended hereto.

DETAILED DESCRIPTION OF EMBODIMENT(S) OF THE INVENTION

The subject matter of the invention thus is an improved hardener for silicone rubber materials, the use of the hardener according to the invention for curing silicone rubber materials, a composition including the hardener, the use thereof, and a method of preparing the hardener.

More specifically, the subject matter of the invention is a hardener for silicone rubber materials, comprising at least one compound having the general formula $Si(R^1)_3R^2$ (I), wherein the radicals $R^1$ are 2-hydroxy-propionic acid alkyl ester radicals having the general formula —OCH(CH$_3$)COOR, radical R is a straight-chain or branched alkyl radical, optionally substituted, having from 1 to 4 carbon atoms, and radical $R^2$ is selected from the group consisting of a straight-chain or branched alkenyl radical, optionally substituted, having at least two carbon atoms.

In general formula (I) the term used to specify the radical $R^1$, namely "2-hydroxy-propionic acid alkyl ester radical" means a substituent of the silane compound (I) obtained by condensation of a corresponding silanol compound with a molecule of 2-hydroxy-propionic acid alkyl ester (also referred to as lactic acid alkyl ester or alkyl lactate), a Si—O bond forming between the central silicon atom of the silane compound and the oxygen atom of the free hydroxy function of the 2-hydroxy-propionic acid which is esterified with an alcohol. The 2-hydroxy-propionic acid alkyl ester radical $R^1$ is represented by the general formula —OCH(CH$_3$)COOR, wherein radical R is a straight-chain or branched alkyl radical, optionally substituted, having from 1 to 4 carbon atoms. The alkyl radical R preferably is a methyl, ethyl, propyl, or isopropyl radical, an ethyl radical being especially preferred. Accordingly, the radical $R^1$ preferably is a 2-hydroxy-propionic acid methyl ester radical, a 2-hydroxy-propionic acid ethyl ester radical, a 2-hydroxy-propionic acid propyl ester radical, or a 2-hydroxy-propionic acid isopropyl ester radical. Especially preferred is an $R^1$ radical which is a 2-hydroxy-propionic acid ethyl ester radical (ethyl lactato radical).

Within the meaning of the present invention, the term "2-hydroxy-propionic acid alkyl ester radical" comprises all stereo isomers (enantiomers) of the corresponding 2-hydroxy-propionic acid alkyl ester, especially the pure (R)-2-hydroxy-propionic acid alkyl ester and the pure (S)-2-hydroxy-propionic acid alkyl ester, as well as mixtures thereof, including a racemic mixture. Within the meaning of the present invention, for example, the 2-hydroxy-propionic acid ethyl ester comprises the pure (R)-2-hydroxy-propionic acid ethyl ester (D-(+)-lactic acid ethyl ester) and the pure (S)-2-hydroxy-propionic acid ethyl ester (L-(−)-lactic acid ethyl ester) and mixtures thereof, including a racemic mixture.

The alkyl esters of 2-hydroxy-propionic acid (lactic acid), in general, are characterized by preferred properties such as odor, stability, compatibility, etc. The ethyl ester ("ethyl lactate"), for example, has a mild fruity scent. The ethyl ester of 2-hydroxy-propionic acid (lactic acid ethyl ester or ethyl lactate), furthermore, is an approved food additive. The 2-hydroxy-carboxylic acid is a natural and metabolic product, respectively, and as such not harmful to a human organism or an animal or plant organism. The same is true of its ethyl ester.

The hardener according to the invention is a neutrally cross-linking hardener for silicone rubber materials and has many advantages, contrary to the customary hardeners; it may be used in place of conventional hardeners. It is advantageous that the compound which has the general formula (I) releases only 2-hydroxy-propionic acid alkyl ester (alkyl lactate) when being hydrolyzed, and this ester is harmless both for the environment and the human and animal organisms, respectively, as well as plants. The ethyl ester of 2-hydroxy-propionic acid (ethyl lactate) even is an approved food additive (cf. Römpp Lexikon Chemie—version 2.0, Stuttgart/New York: Georg Thieme Verlag 1999; bzZitat: Milchsäureethylester (Ethyllactat) and Liste der zugelassenen Lebensmittelzusatzstoffe (Fundstellenliste), Jun. 10, 1992).

The toxicological properties of the leaving group of the hardener according to the invention thus are much better than those of oxime hardeners. Moreover, most people consider the odor of the hardener according to the invention itself and of the silicone rubber materials containing it to be pleasant, something that cannot be said of the rather foul-smelling oxime hardeners. The pleasant scent of the hardener according to the invention is transmitted also to sealing compounds prepared using the hardener. In addition, it was found, surprisingly, that compounds having the general formula (I) and including 2-hydroxy-propionic acid ethyl ester radicals impart especially advantageous properties to a hardener according to the invention, in particular as regards the melting point of the hardener, as well as the storage stability and polymerization rate of the silicone rubber material containing the hardener, and the properties of the resulting polymerization products, such as, for example, adhesiveness or clarity and colorlessness, respectively. This is surprising, particularly in view of the poor properties of neutral cross-linking alkoxy hardeners. After all, in both cases hydroxy groups are components of the bonds split by hydrolysis. The hardener according to the invention is clearly superior to customary alkoxy hardeners, especially in respect of its adhesiveness and storage stability.

In general formula (I) the term "alkenyl radical" designates a molecule radical $R^2$ on the basis of a partly unsaturated aliphatic hydrocarbon compound which comprises at least one C—C double bond. It is preferred that the alkenyl radical comprises one, two, or three C—C double bonds, especially preferred being one C—C double bond. It is preferred that an "alkenyl radical having at least two carbon atoms" comprises from 2 to 8 carbon atoms, further preferred from 2 to 6 carbon atoms, and especially preferred from 2 to 4 carbon atoms. The term "alkenyl radical" comprises both straight-chain and branched hydrocarbon chains. Where branching and/or substitutions of the hydrocarbon chain allow the formation of stereo isomers, especially by the position of the substituents at the carbon atoms of the C—C double bond, the term "alkenyl radical" comprises not only a racemic mixture but also the pure enantiomers and/or diastereomers, as well as mixtures thereof. It is preferred for the "alkenyl radical" to be connected via a Si—C bond to the compound of the general formula (I). The term "alkenyl radical having at least two carbon atoms" especially comprises an allyl radical or a vinyl radical.

According to the invention, the hardener comprises at least one compound of the general formula (I). It is preferred that the hardener according to the invention comprises from 1 to 5 compounds of the general formula (I), further preferred from 1 to 3 compounds of the general formula (I), even more preferred 1 or 2 compounds of the general formula (I), and especially preferred 2 compounds of the general formula (I). The polymerization rate of a silicone rubber material which comprises a hardener according to the invention and, moreover, the properties of the resulting polymerization product can be adjusted to advantage by means of a hardener according to the invention which comprises two, three, or more compounds of the general formula (I). If desired, the hardener according to the invention also may comprise 3, 4, 5, or more compounds of the general formula (I) in order thus to be able to tailor the properties, such as the polymerization rate of a silicone rubber material comprising a hardener according to the invention or the properties of the resulting polymerization product, precisely in accordance with the respective intended usage.

In the presence of water or humidity of the air, the hardener or cross-linking agent for silicone rubber materials according to the invention is able to polymerize or condense, respectively, with difunctional or multifunctional polyorganosiloxane compounds by forming Si—O—Si bonds. Preferred, α,ω-dihydroxy-polyorganosiloxanes are used as difunctional polyorganosiloxanes. Thus a silicone rubber material in the present context preferably means a composition which comprises the hardener and difunctional or multifunctional polyorganosiloxane compounds.

Surprisingly, it was found that the effect of the hardener according to the invention in hardening silicone rubber materials in the presence of water or humidity of the air at room temperature is improved. More particularly, the hardener has the advantage that, upon hydrolysis, it releases an alkyl lactate molecule, preferably an ethyl lactate molecule (2-hydroxy-propionic acid ethyl ester). Ethyl lactate is a harmless compound which, for instance, may be a natural product or a product of metabolism or a derivative thereof. In contrast to hardeners releasing butanone oxime, therefore, the silicone rubber materials produced with a hardener according to the invention are not harmful. Moreover, ethyl lactate is neither corrosive nor in any way aggressive against materials such as metals, mortar, or stone (marble etc.). Besides, the smell of ethyl lactate is pleasant, especially so when compared with all the usual oximes, in particular butanone oxime.

The novel hardener is liquid down to a temperature of −20° C. and can be processed conveniently.

The polymerization products prepared using the hardener according to the invention are free of specks and spots, transparent, and clear.

An alkenyl radical as defined above is the preferred radical $R^2$ of the compound of the general formula (I). It is preferred that the alkenyl radical is an allyl radical or a vinyl radical, especially preferred being a vinyl radical. Given appropriate conditions, an alkenyl radical may cause additional cross-linking with a silicone rubber monomer or polymer which likewise comprises such alkenyl groups. This may lead to polymerization products having exceptionally advantageous properties. Moreover, it was found, surprisingly, that compounds of the general formula (I) which do comprise an alkenyl radical thus defined impart highly advantageous properties to a hardener according to the invention, especially in terms of melting point of the hardener, polymerization rate of silicone rubber material containing the same, and properties of the polymerization product obtained, for instance, its clear and colorless appearance, respectively.

That is surprising particularly because compounds containing, instead of the alkenyl radical $R^2$, a radical, such as an alkyl or aryl radical, in addition to three alkyl lactato radicals, exhibit poor qualities when used purely as hardeners for silicone rubber materials. Investigations have shown that, for instance, alkyl-tris-(ethyl lactato)-silanes, such as methyl-tris-(ethyl lactato)-silane, or ethyl-tris-(ethyl lactato)-silane, or aryl-tris-(ethyl lactato)-silanes, such as phenyl-tris-(ethyl lactato)-silane, when used purely for hardening a silicone rubber material, in particular an RTV silicone rubber material, cause the polymerization rate to be very slow, accompanied by corresponding poor qualities of the polymerization product. That excludes their use as sealing material, for instance. The inventors of the present invention have found that, in contrast to those compounds, the use of hardeners according to the invention in silicone rubber materials brings about good polymerization rates and leads to polymerization products which have especially advantageous properties.

It is especially preferred to select the radical $R^2$ from the group consisting of an allyl radical and a vinyl radical. Particularly preferred is a radical $R^2$ which is a vinyl radical. Hardeners according to the invention including one of these radicals $R^2$ are characterized by having especially advantageous properties.

In an especially preferred embodiment, the hardener according to the invention comprises the compound vinyl-tris-(ethyl lactato)-silane) (formula 1) as the compound of the general formula (I).

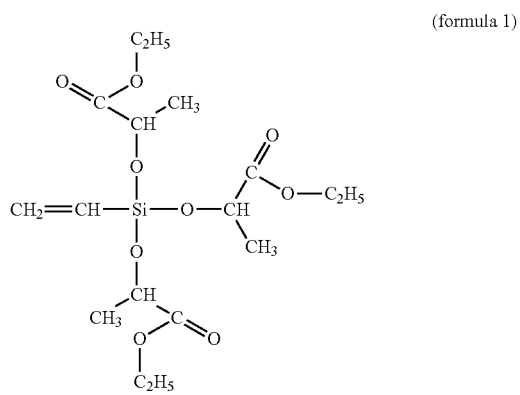

(formula 1)

In a preferred embodiment, the hardener according to the invention comprises at least two compounds which are selected independently of each other from:
a) compounds of the general formula (I) as defined above; and/or
b) compounds having the general formula $Si(R^3)_n R^4_m$ (II), wherein n=1, 2, 3, or 4 and m=(4-n), the radical or radicals $R^3$ being 2-hydroxy-propionic acid alkyl ester radicals of the general formula —OCH(CH$_3$)COOR, radical R being a straight-chain or branched alkyl radical, optionally substituted, having from 1 to 4 carbon atoms, and the radicals $R^4$ being selected independently of each other from the group consisting of a straight-chain or branched alkyl radical, optionally substituted, which has at least one carbon atom, a straight-chain or branched alkenyl radical or alkinyl radical, optionally substituted, which each have at least two carbon atoms, a cycloalkyl radical, optionally substituted, which has at least three carbon atoms, and an aryl radical, optionally substituted, which has at least five carbon atoms.

In general formula (II) the term "2-hydroxy-propionic acid alkyl ester radical" used to define the radical $R^3$ means a substituent of the silane compound (II) obtained by condensation of a corresponding silanol compound with a molecule of a 2-hydroxy-propionic acid alkyl ester (also referred to as lactic acid alkyl ester or alkyl lactate), a Si—O bond forming between the central silicon atom of the silane compound and the oxygen atom of the free hydroxy function of the 2-hydroxy-propionic acid which is esterified with an alcohol. The 2-hydroxy-propionic acid alkyl ester radical $R^3$ is represented by the general formula —OCH(CH$_3$)COOR. Radical R is a straight-chain or branched alkyl radical, optionally substituted, having from 1 to 4 carbon atoms. The alkyl radical R preferably is a methyl, ethyl, propyl, or isopropyl radical, an ethyl radical being especially preferred. Accordingly, the radical $R^3$ preferably is a 2-hydroxy-propionic acid methyl ester radical, a 2-hydroxy-propionic acid ethyl ester radical, a 2-hydroxy-propionic acid propyl ester radical, or a 2-hydroxy-propionic acid isopropyl ester radical. Especially preferred is an $R^3$ radical which is a 2-hydroxy-propionic acid ethyl ester radical.

Within the meaning of the present invention, the term "2-hydroxy-propionic acid alkyl ester radical" comprises all stereo isomers (enantiomers) of the corresponding 2-hydroxy-propionic acid alkyl ester, especially the pure (R)-2-hydroxy-propionic acid alkyl ester and the pure (S)-2-hydroxy-propionic acid alkyl ester, as well as mixtures thereof, including a racemic mixture. Within the meaning of the present invention, for example, the 2-hydroxy-propionic acid ethyl ester comprises the pure (R)-2-hydroxy-propionic acid ethyl ester (D-(+)-lactic acid ethyl ester) and the pure (S)-2-hydroxy-propionic acid ethyl ester (L-(−)-lactic acid ethyl ester) and mixtures thereof, including a racemic mixture.

In general formula (II) the term "alkyl radical" designates a molecule radical $R^4$ on the basis of a saturated aliphatic hydrocarbon compound. It is preferred that an "alkyl radical having at least one carbon atom" comprises a hydrocarbon compound having from 1 to 8 carbon atoms, further preferred from 1 to 6 carbon atoms, further preferred from 1 to 4 carbon atoms, and especially preferred 1 or 2 carbon atoms. The term "alkyl radical" comprises both straight-chain and branched hydrocarbon chains. Where branching and/or substitutions of the hydrocarbon chain allow the formation of stereo isomers, the term "alkyl radical" comprises not only a racemic mixture but also the pure enantiomers and/or diastereomers, as well as mixtures thereof. It is preferred for the "alkyl radical" to be connected via an Si—C bond to the compound of the general formula (II). The term "alkyl radical having at least one carbon atom" especially comprises a methyl radical, an ethyl radical, a propyl radical, an isopropyl radical, a butyl radical, an isobutyl radical, a sec-butyl radical, and a tert-butyl radical.

The terms "alkenyl radical" and "alkinyl radical" each comprise a molecule radical $R^4$ on the basis of a partly unsaturated aliphatic hydrocarbon compound. In the case of the alkenyl radical this comprises at least one C—C double bond, while it comprises at least one C—C triple bond in the case of the alkinyl radical. It is preferred that an "alkenyl radical having at least two carbon atoms" and an "alkinyl radical having at least two carbon atoms", respectively, comprise from 2 to 8 carbon atoms, more preferred from 2 to 6 carbon atoms, and especially preferred from 2 to 4 carbon atoms. The terms "alkenyl radical" and "alkinyl radical", respectively, comprise both straight-chain and branched hydrocarbon chains. Where branching and/or substitutions of the hydrocarbon chain allow the formation of stereo isomers, the terms "alkenyl radical" and "akinyl radical", respectively, comprise not only a racemic mixture but also the pure enantiomers and/or diastereomers, as well as mixtures thereof. It is preferred for the "alkenyl radical" and "alkinyl radical", respectively, to be connected via an Si—C bond to the compound of the general formula (II). The term "alkenyl radical having at least two carbon atoms" especially comprises an allyl radical and a vinyl radical, and the term "alkinyl radical" especially comprises an ethinyl radical (acetylenyl radical).

The term "cycloalkyl radical" designates a molecule radical $R^4$ on the basis of a cyclic, saturated or partly unsaturated aliphatic hydrocarbon compound. A "cycloalkyl radical having at least three carbon atoms" is preferred to comprise from 3 to 8 carbon atoms, further preferred from 3 to 6 carbon atoms, even further preferred from 4 to 6 carbon atoms, and especially preferred 5 or 6 carbon atoms. The term "cycloalkyl radical" also comprises hydrocarbon rings substituted by straight-chain and/or branched hydrocarbon chains. Where branching and/or substitutions of the hydrocarbon ring allow the formation of stereo isomers, the term "cycloalkyl radical" comprises not only a racemic mixture but also the pure enantiomers and/or diastereomers, as well as mixtures thereof. It is preferred for the "cycloalkyl radical" to be connected via an Si—C bond to the compound of the general formula (II). The term "cycloalkyl radical having at least three carbon atoms" especially comprises a cyclopropyl radical, a cyclobutyl radical, a cyclopentyl radical, and a cyclohexyl radical.

In general formula (II) the term "aryl radical" designates a molecule radical $R^4$ on the basis of an aromatic hydrocarbon compound. It is preferred that an "aryl radical having at least five carbon atoms" comprises an aromatic hydrocarbon compound having from 5 to 12 carbon atoms, further preferred from 6 to 12 carbon atoms, and especially preferred from 6 to 10 carbon atoms. In the compound of the general formula (II), the aryl radical having six carbon atoms also may be an unsubstituted phenyl radical as defined above. The term "aryl radical" comprises aromatic ring systems with one, two, three, or more rings which may be interconnected either by C—C single bonds or by common edges. The "aryl radical" is preferred to be connected by an Si—C bond to the compound of the general formula (II). In particular, the term "aryl radical having at least five carbon atoms" comprises a cyclopentadienyl radical, a phenyl radical, a naphthyl radical, and a diphenyl radical.

In accordance with the above definition, the compound of the general formula (II) may comprise exactly one (n=1), two (n=2), three (n=3), or four (n=4) 2-hydroxy propionic acid alkyl ester radicals, 2-hydroxy propionic acid ethyl ester radicals being preferred, and accordingly three (m=3 with n=1), two (m=n=2), and one (m=1 with n=3) radical(s) $R^4$, respectively, being included. Where a compound of the general formula (II) comprises two or three radicals $R^4$, they may differ from one another, i.e. they may be selected independently from an alkyl radical having at least one carbon atom, an akenyl radical and an akinyl radical each having at least two carbon atoms, a cycloalkyl radical having at least three carbon atoms, and an aryl radical having at least five carbon atoms.

In a preferred embodiment of the compound of the general formula (II), there is n=3 and m=1 or n=m=2, i.e. the compound of the general formula (II) comprises not only 2-hydroxy propionic acid alkyl radicals $R^3$ but also one or two additional radicals $R^4$ in accordance with the above definition. Especially preferred as radical $R^4$ of the compound of the general formula (II) is an alkyl or alkenyl radical as defined above. Especially preferred, the radical $R^4$ is selected from methyl, ethyl, propyl, isopropyl, butyl, isobutyl, sec-butyl, tert-butyl, allyl, vinyl, cyclopentyl, cyclohexyl, phenyl, and diphenyl radicals, and very particularly preferred from methyl, ethyl, vinyl, phenyl, and isopropyl radicals. Under appropriate conditions, a vinyl radical may cause cross-linking with a silicone rubber monomer or polymer, respectively, which likewise contain such alkenyl groups. In this way polymerization products may be obtained which have particularly advantageous properties. In another preferred embodiment, the compound of the general formula (II) with n=m=2 comprises two different radicals $R^4$ which are selected independently of each other from the radicals $R^4$ listed above. It is preferred that such a compound of the general formula (II) comprises an alkyl radical and an alkenyl radical, such as an ethyl radical and a vinyl radical, or an alkyl radical and an aryl radical, such as an ethyl radical and a phenyl radical.

Hardeners according to the invention including one or two of these radicals $R^4$ are characterized by especially advantageous properties. It was found, surprisingly, that compounds of the general formula (II) which comprise one or two of the radicals $R^4$ thus defined impart a hardener according to the invention with particularly advantageous properties, especially as regards the melting point of the hardener, the polymerization rate of a silicone rubber material containing this hardener, and the properties of the polymerization product obtained, for instance, its clarity and colorlessness.

In an alternative preferred embodiment of the compound of the general formula (II), there is n=4 (and accordingly m=0), i.e. the compound of the general formula (II) comprises only 2-hydroxy-propionic acid alkyl radicals, preferably only 2-hydroxy-propionic acid ethyl radicals ($R^3$) and no other radicals $R^4$. This compound of the general formula (II) imparts the hardener according to the invention with the property to provide especially highly cross-linked silicone rubber materials. A preferred example of this embodiment of the compound of the general formula (II) is the compound tetra-(ethyl lactato)-silane.

In the embodiment described above, the hardener according to the invention comprises at least two different compounds which are selected independently from
a) compounds of the general formula (I) and/or
b) compounds of the general formula (II).

It is preferred for the hardener to comprise at least two compounds of the general formula (I), or at least two compounds of the general formula (II), or at least one compound of the general formula (I) and at least one compound of the general formula (II). Further preferred is a hardener according to the invention including at least two compounds of the general formula (I), or at least one compound of the general formula (I) and at least one compound of the general formula (II). Especially preferred is a hardener according to the invention which comprises two compounds of the general formula (I), or one compound of the general formula (I) and one compound of the general formula (II), or one compound of the general formula (I) and two compounds of the general formula (II).

A hardener according to the invention which comprises at least two different compounds selected independently of each other from compounds of the general formula (I) and/or compounds of the general formula (II) offers the advantage that both the polymerization rate of a silicone rubber material containing a hardener according to the invention and the properties of the resulting polymerization product can be adjusted. If desired, the hardener of the invention may comprise mixtures of 2, 3, 4, 5, or more compounds of the general formulae (I) and/or (II). By these means, properties can be custom-designed according to the requirements of the respective intended application, such as the polymerization rate of a silicone rubber material which comprises a hardener according to the invention, or the properties of the resulting polymerization product. Surprisingly, it was found that the effect of the hardener according to the invention in curing silicone rubber materials in the presence of water or moisture of the air at room temperature is improved. More specifically, it also has the advantage that the hydrolysis releases nothing but alkyl lactate molecules, such as ethyl lactate molecules (2-hydroxy-propionic acid ethyl ester molecules). Since the novel hardener is liquid down to a temperature of −20° C., it can be manipulated with ease.

The polymerization products made with the use of a hardener according to the invention are free of specks and spots, and they are transparent, and clear.

In a preferred further embodiment the hardener according to the invention comprises at least one compound of the general formula (I) and in addition at least one compound, different from the first, of the general formula (II). It is preferred for the hardener according to the invention to comprise one, two, or three compounds of the general formula (I) and one, two, or three compounds, differing from them, of the general formula (II). Especially preferred, the hardener comprises a compound of the general formula (I) and, additionally, a compound of the general formula (II), or a compound of the general formula (I) and, additionally, two compounds of the general formula (II). As a compound of the general formula (I), for example, the hardener may comprise vinyl-tris-(ethyl lactato)-silane and methyl-tris-(ethyl-lactato)-silane as a compound of the general formula (II). Or the compound of the general formula (I) may be vinyl-tris-(ethyl-lactato)-silane and there may be two compounds of the general formula (II), namely methyl-tris-(ethyl lactato)-silane and tetra-(ethyl lactato)-silane.

A hardener according to the invention comprising not only one compound of the general formula (I) but additional also at least one compound of the general formula (II) allows the advantageous adjustment of the polymerization rate of a silicone rubber material which comprises a hardener according to the invention and also of the properties of the resulting polymerization product. If desired, the hardener according to the invention in addition may comprise 1, 2, 3, or more compounds of the general formula (II) in order thus to be able to tailor the properties, such as the polymerization rate of a silicone rubber material comprising a hardener according to the invention or the properties of the resulting polymerization product precisely in accordance with the respective intended usage.

It was found, surprisingly, that the effect in curing silicone rubber materials at room temperature in the presence of water or humidity of the air is improved still further if the hardener according to the invention in addition comprises at least one compound of the general formula (II). Moreover, the hardener according to the invention has the advantage that the hydrolysis releases only alkyl lactate molecules, such as ethyl lactate molecules (2-hydroxy-propionic acid ethyl ester molecules).

The novel hardener is liquid down to a temperature of −20° C. and, therefore, can be handled conveniently. The polymerization products made with the use of the hardener according to the invention are free of specks and spots, and they are transparent and clear.

In an especially preferred embodiment the hardener according to the invention comprises not only a compound of the general formula (I) but also at least one compound of the general formula (II) in which the radical(s) $R^4$ is (are) alkyl radical(s), and especially preferred, at least one compound of the general formula (II) in which the radical(s) $R^4$ is (are) alkyl radical(s) and the radical(s) $R^3$ is (are) ethyl lactato radical(s).

In another especially preferred embodiment the hardener according to the invention, additionally, comprises at least one compound of the general formula (II) selected from methyl-tris-(ethyl lactato)-silane (formula 2), ethyl-tris-(ethyl lactato)-silane (formula 3), and tetra-(ethyl lactato)-silane (formula 4).

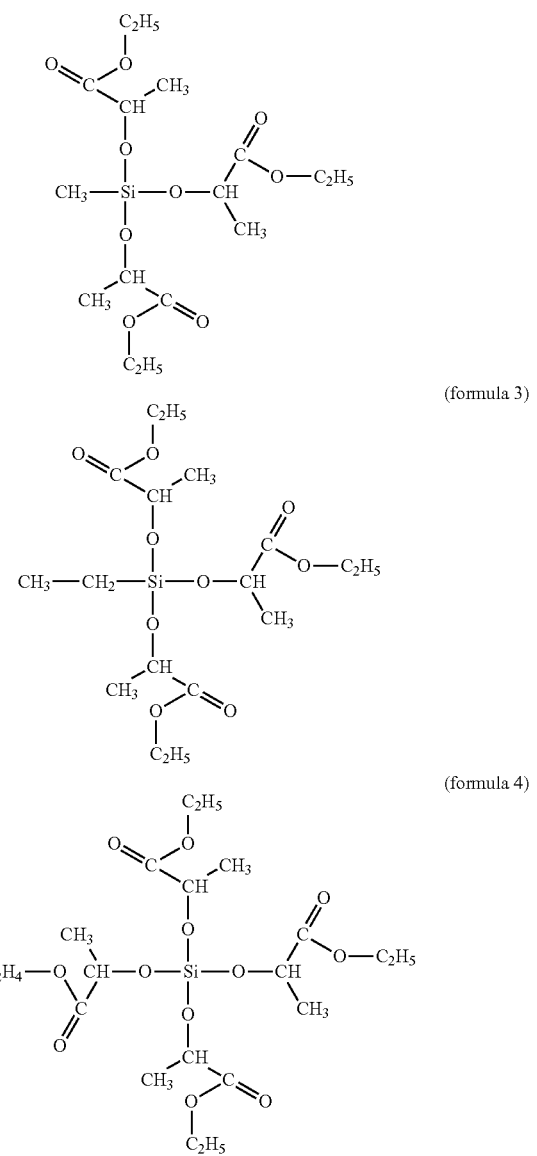
(formula 2)
(formula 3)
(formula 4)

A hardener according to the invention comprising, in addition, also methyl-tris-(ethyl lactato)-silane and/or ethyl-tris-(ethyl lactato)-silane and/or tetra-(ethyl lactato)-silane imparts a further improved effect in curing silicone rubber materials in the presence of water or humidity of the air. It has all the positive properties mentioned above, including the fact that hydrolysis of the compounds having formulae (2), (3), and (4) releases nothing but the harmless ethyl lactate. Since also the compound of the general formula (I), when hydrolyzed, releases only ethyl lactate, a hardener of this kind according to the invention releases nothing but ethyl lactate. Moreover, the properties which the hardener will have upon curing (e.g. skin formation time, tack free time, early strain, etc.) can be fine-tuned by corresponding selection of the percentages of its components. Especially preferred is a hardener which comprises methyl-tris-(ethyl lactato)-silane besides vinyl-tris-(ethyl lactato)-silane, and a hardener which comprises methyl-tris-(ethyl lactato)-silane and tetra-(ethyl lactato)-silane besides vinyl-tris-(ethyl lactato)-silane.

It is preferred in this context that the hardener comprises a compound of the general formula (I) in a content of from 20 to 80% by weight, further preferred from 30 to 70% by weight, and even further preferred from 30 to 50% by weight, and especially preferred 30 or 50% by weight. In addition, the hardener preferably comprises at least one compound of the general formula (II) in a content of from 20 to 80% by weight, further preferred from 30 to 75% by weight, even further preferred from 50 to 70%, and especially preferred 50 or 70% by weight. Apart from the above, the hardener may comprise further cross-linkable compounds on the basis of compounds having the general formulae (I) or (II). In an especially preferred embodiment the hardener according to the invention comprises 50% by weight of a compound of the general formula (I) and 50% by weight of a compound of the general formula (II). An example of this embodiment is a hardener according to the invention which comprises 50% by weight of methyl-tris-(ethyl lactato)-silane and 50% by weight of vinyl-tris-(ethyl lactato)-silane. In another preferred embodiment the hardener according to the invention comprises 30% by weight of a compound of the general formula (I) and 70% by weight of a compound of the general formula (II). An example of this embodiment is a hardener according to the invention comprising 70% by weight of methyl-tris-(ethyl lactato)-silane and 30% by weight of vinyl-tris-(ethyl lactato)-silane. An example of a hardener according to the invention comprising more than one compound of the general formula (II) is a hardener which comprises 40-45% by weight of vinyl-tris-(ethyl lactato)-silane, 40-45% by weight of methyl-tris-(ethyl lactato)-silane, and 10-20% by weight of tetra-(ethyl lactato)-silane.

In accordance with the invention, the hardener according to the invention is used for curing a silicone rubber material. To this end a composition is prepared, within the meaning of the present invention, that comprises the hardener according to the invention and an appropriate silicone rubber material (silicone rubber mass) or the precursors thereof, respectively.

Thus a composition according to the invention comprises the hardener according to the invention specified above and at least one organosilicone compound, preferably the hardener according to the invention described plus two, three, or more different organosilicone compounds. One organosilicone compound contained in the composition preferably is an oligomeric or polymeric compound. The polymeric organosilicone compound preferably is a difunctional polyorganosiloxane compound, especially preferred is an $\alpha,\omega$-dihydroxyl-terminated polyorganosiloxane. Especially preferred are $\alpha,\omega$-dihydroxyl-terminated polydiorganosiloxanes, particularly $\alpha,\omega$-dihydroxyl-terminated polydialkylsiloxanes, $\alpha,\omega$-dihydroxyl-terminated polydialkenylsiloxanes, or $\alpha,\omega$-dihydroxyl-terminated polydiarylsiloxanes. Apart from homopolymeric $\alpha,\omega$-dihydroxyl-terminated polydiorganosiloxanes, heteropolymeric $\alpha,\omega$-dihydroxyl-terminated polyodiorganosiloxanes, which have different organic substituents, also may be used. These comprise both copolymers of monomers with similar or identical organic substituents on a silicon atom and also copolmyers of monomers with different organic substituents on a silicon atom, for example those including mixed alkyl, alkenyl, and/or aryl substituents. The preferred organic substituents comprise straight-chain and branched alkyl groups having from 1 to 8 carbon atoms, especially methyl, ethyl, n-propyl and isopropyl, as well as n-butyl, sec-butyl, and tert-butyl, vinyl, and phenyl. Individual ones or all of the carbon-bound hydrogen atoms within the individual organic substituents may be substituted by conventional substituents, such as halogen atoms, or functional groups, such as hydroxyl- and/or amino groups. Thus it is possible to use α,ω-dihydroxyl-terminated polydiorganosiloxanes having partly fluorinated or perfluorinated organic substituents, or α,ω-dihydroxyl-terminated polydiorganosiloxanes, the silicon atoms of which have organic substituents that are substituted by hydroxyl- and/or amino groups.

Especially preferred examples of an organosilicon compound are α,ω-dihydroxyl-terminated polydialkylsiloxanes, such as α,ω-dihydroxyl-terminated polydimethylsiloxanes or α,ω-dihydroxyl-terminated polydiethylsiloxanes, or α,ω-dihydroxyl-terminated polydivinylsiloxanes, as well as α,ω-dihydroxyl-terminated polydiarylsiloxanes, such as α,ω-dihydroxyl-terminated polydiphenylsiloxanes. Those polyorganosiloxanes having a kinematic viscosity of from 5,000 to 120,000 cSt (at 25° C.) are the preferred ones, in particular those having a viscosity of from 20,000 to 100,000 cSt, especially preferred being those having a viscosity of from 40,000 to 90,000 cSt.

Mixtures comprising polydiorganosiloxanes, which have different viscosities, may also be used.

If desired, the composition according to the invention may comprise other conventional additives in addition. Usual additives are fillers, colorants, softeners, thixotropic agents, wetting agents, adhesion promoters, catalysts, and others.

Both reinforcing as well as non-reinforcing fillers may be used as fillers. The preferred fillers are inorganic fillers, for instance, highly disperse, pyrogenic, or precipitated silicic acids, carbon black, quartz powder, chalk, or metal salts or metal oxides, such as titanium oxides. An especially preferred filler is a highly disperse silicic acid, for example, a commercial filler obtainable from Cabot under the name of Cabosil 150. Fillers like highly disperse silicic acids, especially pyrogenic silicic acids, are also useful as thixotropic agents. Metal oxides are useful also as colorants; titanium oxides, for example, as a white colorant. Moreover, the fillers may be surface modified by known methods, for example, silicic acids made hydrophobic with silanes can be used.

Suitable softeners are per se known polydiorganosiloxanes without functional terminal groups, which are therefore different from the organosilicone compounds used according to the invention. And/or liquid aliphatic or aromatic hydrocarbons may be used, preferably those having molecular weights from about 50 to about 5000, whose volatility is low and which are sufficiently compatible with polysiloxanes. The preferred kinematic viscosity of softeners is from 1 to 5,000 cSt (at 25° C.), in particular from 50 to 500 cSt, especially preferred being from 90 to 200 cSt. Examples of softeners comprise polydimethylsiloxanes having a viscosity of from 90 to 120 cSt, especially of 100 cSt, paraffin oils, and polysubstituted alkylbenzenes.

The preferred wetting agents and/or adhesion promoters (coupling agents) used are per se known silane compounds with organic substituents carrying reactive groups on the silicon atom, which differ from the organosilicone compounds used according to the invention, such as organosilanes having reactive amine groups, carboxylic acid groups, epoxy groups, or thiol groups. Among the preferred examples there are aminosilanes, such as aminoethyl-aminopropyl-trialkoxysilane. Concrete examples of preferred adhesion promoters (coupling agents) are 3-aminopropyl-triethoxysilane, 3-aminopropyl-trimethoxysilane, aminoethyl-aminopropyl-trimethoxysilane, butylaminopropyl-triethoxysilane, butylaminopropyl-trimethoxysilane, propylaminopropyl-triethoxysilane, propylaminopropyl-trimethoxysilane, N-cyclohexyl-3-aminopropyl-trimethoxysilane, N-cyclohexyl-3-aminopropyl-triethoxysilane, and co-oligomeric diamino/alkyl functional silane which is commercially available as Dynasylan 1146 from Degussa.

It is preferred to use metalorganic catalysts as employed usually for condensation-cross-linking polysiloxanes. Preferred catalysts are tin-organic compounds, such as dibutyl tin laurate, dibutyl tin diacetate, and tin(II)-octoate. Especially preferred catalysts are alkyl-tin-carboxylates, for instance, dibutyl tin difaurate, dibutyl tin divaleriate, dibutyl tin diacetate, dibutyl tin dineodecanoate, dibutyl tin diacetylacetonate, dioctyl tin-bis-(2-ethylhexanoate), dibutyl tin dimaleate, and butyl tin-tris-(2-ethylhexanoate). Titanium-based, zirconium-based, or aluminum-based compounds also may be used as catalysts.

It was found that the composition may be stored for periods of more than 12 months under exclusion of moisture, and that it polymerizes at room temperature under the influence of water or humidity of the air.

Furthermore, it is advantageous that the composition according to the invention, when being cured to form a silicone rubber material, releases only 2-hydroxy-propionic acid alkyl esters, such as 2-hydroxy-propionic acid ethyl ester (ethyl lactate) which, in contrast to oxime compounds, e.g. butan-2-one oxime, is not a health hazard, nor is it corrosive or aggresive against such materials as metals, mortar, or stone (marble etc.), and its scent is pleasant. The fully hardened material is free of specks and spots and it is transparent and clear.

The composition according to the invention is preferred to comprise from 40 to 90% by weight of the organosilicone compound and from 1 to 15% by weight of the hardener according to the invention, the remainder being made up of conventional additives. Likewise preferred is a composition which comprises from 50 to 80% by weight of the organosilicone compound and from 1 to 15% by weight of the hardener according to the invention, especially preferred being from 50 to 70% by weight of the organosilicone compound and from 3 to 10% by weight of the hardener according to the invention, the remainder being made up of conventional additives.

The subject matter of the invention also resides in the use of the composition according to the invention as a sealant, adhesive, or coating agent or material. The composition finds preferred application in the construction sector, specifically as a sealant or adhesive, especially for joints in buildings and civil engineering projects, for glass elements and windows (preferred) and in sanitary installations. Mechanical engineering likewise is open for use of the composition, e.g. the motor vehicle sector (preferred), electronics and textile industries, and industrial plants and installations.

Another subject matter of the invention is a method of preparing a hardener according to the invention. The method according to the invention relates particularly to preparing a compound of the general formula (I). A compound of the general formula (I) is prepared by the method according to the invention in that a compound having the general formula $SiX_3R^2$ (III) is reacted with three equivalents of 2-hydroxy-propionic acid alkyl ester, preferably 2-hydroxy-propionic acid ethyl ester (ethyl lactate). Radical $R^2$ in the compound of the general formula (III) is selected from an alkenyl radical, the respective radicals being defined as described above. Radical X (the leaving group or group released) in the compound of the general formula (III) is selected from a usual leaving group which reacts with a free hydroxy function of another molecule, such as, for example, an alcohol having the general formula R'—OH, which reacts under release of the H—X molecule, whereby an Si—O—R' bond is formed between the silicon atom of the compound of the general formula (III) and the molecule radical added. The leaving group X is preferred to be an alkoxy radical having at least one carbon atom or a halogen atom, especially a chlorine atom.

A compound of the general formula (II) may be produced by an analogous method, if a respective compound having the general formula $SiX_n(R^4)_m$ (IV), wherein n=1, 2, 3, or 4, and m=(4−n), is reacted with n equivalents of 2-hydroxy-propionic acid alkyl ester, preferably 2-hydroxy-propionic acid ethyl ester (ethyl lactate), the radicals X and $R^4$ having the definitions specified above.

EXAMPLES

Example 1

General Synthesis of a Compound of the Formula (I)

Under an atmosphere of nitrogen, 500.0 g of ethyl lactate (4.23 mol), 1500.0 g of toluene and 432.6 g of triethylamine (4.27 mol) are placed in a 4000 ml four-necked flask, equipped with a stirrer (KPG-Rthrer), dripping funnel, condenser, thermometer and water cooling bath. Afterwards, 226.1 g of vinyltrichlorosilane (1.40 mol) are added under cooling by water bath so that the temperature does not exceed 30° C. After completion of the addition, the mixture is stirred for 3 hours at room temperature, and the resulting solid is subsequently filtered and washed with toluene. The combined filtrates are placed in a destillation apparatus and the solvent toluene is removed under vacuum.

If necessary, the product may also be destilled.

Conditions: sump temperature 160° C., head temperature 126° C., vacuum 1-2 mbar

Yield: 529.0 g of vinyl-tris-(ethyl lactato)-silane having a purity of 92.5% as determined by GC. This corresponds to a yield of 93% of the theoretical, based on vinyltrichlorosilane.

A capillary gas chromatograph (Capillary GC) with a column having a length of 25 m and an inner diameter (ID) of 0.25 mm (FD: 0.5 um) and a FID-detector was used for the determination of the purity of the prepared hardener compounds of the general formulae (1) and (II). Helium was used as carrier gas and the split was 150 ml/min. The samples were introduced without sample preparation via a direct injection system with a sample amount of 0.3 µl.

Example 2

General Synthesis of a Compound of the Formula (II)

Under an atmosphere of nitrogen, 500.0 g of ethyl lactate (4.23 mol), 1500.0 g of toluene and 432.6 g of triethylamine (4.27 mol) are placed in a 4000 ml four-necked flask, equipped with a stirrer (KPG-Rührer), dripping funnel, condenser, thermometer and water cooling bath. Afterwards, 209.0 g of methyltrichlorosilane (1.40 mol) are added under cooling by water bath so that the temperature does not exceed 30° C. After completion of the addition, the mixture is stirred for 3 hours at room temperature, and the resulting solid is subsequently filtered and washed with toluene. The combined filtrates are placed in a destillation apparatus and the solvent toluene is removed under vacuum.

If necessary, the product may also be destilled.

Conditions: sump temperature 160° C., head temperature 130° C., vacuum 1-2 mbar

Yield: 502.0 g of methyl-tris-(ethyl lactato)-silane having a purity of 93% as determined by GC (cf. example 1). This corresponds to a yield of 91% of the theoretical, based on methyltrichlorosilane.

Ethyl-tris-(ethyl lactato)-silane is prepared in an analogous synthesis, except that 228.9 g of ethyltrichlorosilane (1.40 mol) are added. Yield: 537.6 g of ethyl-tris-(ethyl lactato)-silane having a purity of 93.5% as determined by GC (cf. example 1). This corresponds to a yield of 94% of the theoretical, based on ethyltrichlorosilane.

The preparation of phenyl-tris-(ethyl lactato)-silane is carried out in an analoguous manner.

Tetra-(ethyl lactato)-silane is prepared in an analogous synthesis, except that 237.9 g of tetrachlorosilane (1.40 mol) are added and 668.1 g of ethyl lactate (5.66 mol) are used.

Yield: 650 g of tetra-(ethyl lactato)-silane having a purity of 94.0% as determined by GC (cf. example 1). This corresponds to a yield of 93.5% of the theoretical, based on tetrachlorosilane.

Example 3 and Comparative Examples 1 to 4

Sealants with a Hardener Having the Formula (I) or (II)

A silicone rubber basic mixture is prepared according to the following formulation:

585.0 g of α,ω-dihydroxyl-terminated polydimethylsiloxane having a viscosity of 80,000 cSt
260.0 g of polydimethylsiloxane having a viscosity of 100 cSt
90.0 g of highly disperse silicic acid (Cabosil 150)
10.0 g of coupling agent (aminoalkyl-trialkoxysilane)
0.2 g of catalyst (alkyl-tin-carboxylate)

In each case, 40 g of a compound of the formula (I) (example 3) or of a compound of the formula (II) (comparative examples 1 to 4) are added as hardener as follows:

Example 3: vinyl-tris-(ethyl lactato)-silane
Comparative example 1: methyl-tris-(ethyl lactato)-silane
Comparative example 2: ethyl-tris-(ethyl lactato)-silane
Comparative example 3: phenyl-tris-(ethyl lactato)-silane
Comparative example 4: tetra-(ethyl lactato)-silane After exposure to air, the properties skin formation time, tack free time and complete cure are determined according to usual methods. All measurements were carried out under conditions of 23° C. and 50% humidity.

The results are shown in Table 1.

TABLE I

| Nr. | skin formation time (min) | tack free time (min) | complete cure (h) |
| --- | --- | --- | --- |
| Example 3 | 2 | 10 | 10 |
| Comparative example 1 | 120 | >1000 | >96 |
| Comparative example 2 | 110 | >1000 | >96 |
| Comparative example 3 | 90 | >1000 | >96 |
| Comparative example 4 | —* | —* | —* |

*could not be measured because the sealant already cured in the cartridge upon mixing with the silicone rubber basic mixture.
skin formation time: time, at which a complete layer of solidified material (skin) was observed on the surface of a sample strand.
tack free time (Klebfreizeit): time, at which the surface of a sample strand does no longer exhibit tackiness (adherence).
complete cure: application of the sealant on glas with a height of 4 mm; time period until curing to the glas surface.

It is apparent from the results in Table 1 that the hardener according to the invention in example 3 results in a sealant having usable properties. In contrast thereto, the hardeners in the comparative examples 1 to 4 do not result in usable sealants. The sealants of the comparative examples 1, 2 and 3 have a very long skin formation time and their tack free time and complete cure are longer than acceptable for a sealant. The measurements were terminated after 1000 min (tack free time) and 96 h (complete cure), respectively, since sealants having properties outside these ranges are not usable. In comparative example 4, the mixing of the hardener with the silicone rubber basic mixture already lead to a complete cure, so that this sealant could not be processed.

Examples 4 to 6 and Comparative Examples 5 to 7

Sealants with Two Hardeners Having the Formula (I) and/or (II)

A silicone rubber basic mixture is prepared with a formulation as described in example 3.

In each case, 40 g of a mixture of a compound of formula (I) and a compound of formula (II) (examples 4 to 6), or of a mixture of two compounds of the formula (II) (comparative examples 5 to 7), respectively, are added as hardener as follows:

Example 4: 50% vinyl-tris-(ethyl lactato)-silane
  50% methyl-tris-(ethyl lactato)-silane
Example 5: 50% vinyl-tris-(ethyl lactato)-silane
  50% ethyl-tris-(ethyl lactato)-silane
Example 6: 50% vinyl-tris-(ethyl lactato)-silane
  50% phenyl-tris-(ethyl lactato)-silane
Comparative example 5: 50% methyl-tris-(ethyl lactato)-silane
  50% ethyl-tris-(ethyl lactato)-silane
Comparative example 6: 50% methyl-tris-(ethyl lactato)-silane
  50% phenyl-tris-(ethyl lactato)-silane
Comparative example 7: 50% methyl-tris-(ethyl lactato)-silane
  50% tetra-(ethyl lactato)-silane After exposure to air, the properties skin formation time, tack free time and complete cure are determined according to usual methods. All measurements were carried out under conditions of 23° C. and 50% humidity.

The results are shown in Table 2.

TABLE 2

| Nr. | skin formation time (min) | tack free time (min) | complete cure (h) |
| --- | --- | --- | --- |
| Example 4 | 12 | 60 | 24 |
| Example 5 | 10 | 50 | 24 |
| Example 6 | 7 | 40 | 20 |
| Comparative example 5 | 120 | >1000 | >96 |
| Comparative example 6 | 110 | >1000 | >96 |
| Comparative example 7 | —* | —* | —* |

*could not be measured because the sealant already cured in the cartridge upon mixing with the silicone rubber basic mixture.
skin formation time: time, at which a complete layer of solidized material (skin) was observed on the surface of a sample strand.
tack free time (Klebfreizeit): time, at which the surface of a sample strand does no longer exhibit tackiness (adherence).
complete cure: application of the sealant on glas with a height of 4 mm; time period until curing to the glas surface.

It is apparent from the results in Table 2 that the hardener according to the invention in examples 4, 5 and 6 results in a sealant having excellent properties, which are comparable to those of conventional sealants. Usually, the following properties are desired for silicone sealants: a skin formation time of from 5 to 15 minutes, a tack free time of from 60 to 120 minutes, and a complete cure of 48 hours maximum.

In contrast thereto, the hardeners in the comparative examples 5 to 7 do not result in usable sealants. The sealants of the comparative examples 5 and 6 have a very long skin formation time and their tack free time and complete cure are longer than acceptable for a sealant. The measurements were terminated after 1000 min (tack free time) and 96 h (complete cure), respectively, since sealants having properties outside these ranges are not usable. In comparative example 7, the mixing of the hardener with the silicone rubber basic mixture already lead to a complete cure, so that this sealant could not be processed.

Example 7

Sealant Formulation A

A silicone rubber mixture is prepared according to the following formulation:
585.0 g of α,ω-dihydroxyl-terminated polydimethylsiloxane having a viscosity of 80,000 cSt
260.0 g of polydimethylsiloxane having a viscosity of 100 cSt
  90.0 g of highly disperse silicic acid (Cabosil 150)
  10.0 g of coupling agent (aminoalkyl-trialkoxysilane)
    0.2 g of catalyst (alkyl-tin-carboxylate)

A mixture according to the following formulation is added as hardener A:
  20.0 g of vinyl-tris-(ethyl lactato)-silane
  20.0 g of methyl-tris-(ethyl lactato)-silane The sealant exhibits after exposure to air:
a skin formation time of 12 min
a tack free time of 60 min
an early strain after 70 min
a complete cure after 24 h
a transparent appearence
a pleasant odor
a Shore-hardness A of 22

The properties skin formation time, tack free time, early strain, complete cure, appearance, odor and shore-hardness A were determined according to usual methods. All measurements were carried out at conditions of 23° C. and 50% humidity.

For the determination of the skin formation time, the time was measured, at which a complete layer of solidified material (skin) was detected on the surface of a sample strand.

For the determination of the tack free time (Klebfreizeit), the time was measured, at which the surface of a sample strand no longer exhibits tackiness (adherence).

For the determination of the early strain, a silicone strip having a height of 10 mm was applied to a sheet metal strip. The resilience (strain) is tested by bending the strip by 90°. The time is recorded, at which the skin of the silicone strip does not crack.

For the determination of the complete cure, the sealant is applied to a glas plate with a height of 4 mm, and the time period is measured until complete curing to the glas plate.

Appearance and odor are determined by organo-leptic tests.

The Shore-hardness A was determined using a measuring device "Zwick-Roell-Messgerat" (Bez.: ASTM D 2240; DIN 53505; ISO 868).

Example 8

Sealant Formulation B

A silicone rubber mixture is prepared according to the following formulation:
585.0 g of α,ω-dihydroxyl-terminated polydimethylsiloxane having a viscosity of 80,000 cSt
260.0 g of polydimethylsiloxane having a viscosity of 100 cSt
  90.0 g of highly disperse silicic acid (Cabosil 150)
  10.0 g of coupling agent (aminoalkyl-trialkoxysilane)
    0.2 g of catalyst (alkyl-tin-carboxylate)

A mixture according to the following formulation is added as hardener B:
17.5 g of vinyl-tris-(ethyl lactato)-silane
17.5 g of methyl-tris-(ethyl lactato)-silane
5.0 g of tetra-(ethyl lactato)-silane
The sealant exhibits after exposure to air:
a skin formation time of 11 min
a tack free time of 50 min
an early strain after 60 min
a complete cure after 24 h
a transparent appearance
a pleasant odor
a Shore-hardness A of 24
Measurement conditions were as described in example 7.

Comparative Example 8

Sealant Formulation with Oxime Hardener (2-butanone oxime/MEKO)
A silicone rubber mixture is prepared according to the following formulation:
585.0 g of α,ω-dihydroxyl-terminated polydimethylsiloxane having a viscosity of 80,000 cSt
260.0 g of polydimethylsiloxane having a viscosity of 100 cSt
90.0 g of highly disperse silicic acid (Cabosil 150)
10.0 g of coupling agent (aminopropyl-triethoxysilane)
0.2 g of catalyst (alkyl-tin-carboxylate)
A mixture according to the following formulation is added as hardener:
13.5 g of vinyl-tris-(2-butanone oximo)-silane (VOS)
32.0 g of methyl-tris-(2-butanone oximo)-silane (MOS)
The sealant exhibits after exposure to air:
a skin formation time of 13 min
a tack free time of 55 min
an early strain after 60 min
a complete cure after 24 h
a transparent appearence
an unpleasant (oxime-like) odor
a Shore-hardness A of 23
Measurement conditions were as described in example 7.

The formulation prepared in comparative example 8 corresponds to a typical formulation of a sealant on basis of a RTV silicone rubber material, which has been adjusted with respect to its properties by many years of optimisation, and is presently used in the art. Upon exposure to air, this sealant releases 2-butanone oxime (MEKO), and therefore is critical from the point of view of the toxicology.

A comparision of the properties of the sealants according to the invention prepared in examples 7 and 8 with those properties of the sealant according to comparative example 8 show that it is possible to prepare sealants with the hardener according to the invention, whose properties correspond to those of the prior art, which are the result of many years of optimisation. The sealants of examples 7 and 8 according to the invention however have the additional advantage that, in contrast to the sealant according to comparative example 8, upon exposure to air, only ethylactate is released, which is not only toxicologically harmless, but also imparts the sealant with a pleasant odor.

The invention claimed is:

1. A hardener for silicone rubber materials, comprising:
a) a compound having the general formula $Si(R^1)_3R^2$ (I), wherein
radicals $R^1$ are 2-hydroxy-propionic acid alkyl ester radicals having the general formula $-OCH(CH_3)COOR$,
radical R is selected from a group consisting of a methyl radical, an ethyl radical, a propyl radical and an isopropyl radical, and
radical $R^2$ is selected from a group comprising at least one of a straight-chain or branched alkenyl radical which has at least two carbon atoms; and
b) a compound having the general formula $Si(R^3)_n R^4_m$ (II), wherein
n=1, 2, 3, or 4 and in (4−n),
radical $R^3$ is a 2-hydroxy-propionic acid alkyl ester radical of the general formula $-OCH(CH_3)COOR$,
radical R is selected from a group consisting of a methyl radical, an ethyl radical, a propyl radical, and an isopropyl radical, and
radical $R^4$ is at least one selected from a group comprising
a straight-chain branched alkyl radical, which has at least one carbon atom,
a straight-chain or branched alkenyl radical or alkinyl radical, which has at least two carbon atoms,
a cycloalkyl radical, which has at least three carbon atoms, and
an aryl radical, which has at least five carbon atoms; and
(c) wherein the compounds of general formulas (I) and (II) are different compounds.

2. The hardener as claimed in claim 1, wherein the radical $R^2$ is at least one selected from a group comprising an allyl radical and a vinyl radical.

3. The hardener as claimed in claim 1, wherein the radical R of general formula (I) is an ethyl radical.

4. The hardener as claimed, in claim 1, wherein the compound a) is vinyl-tris-(ethyl lactato)-silane.

5. The hardener as claimed in claim 1, wherein radical $R^4$ is at least one selected from a group comprising a methyl radical, an ethyl radical, a propyl radical, an isopropyl radical, a butyl radical, an isobutyl radical, a sec-butyl radical, a tert-butyl radical, an allyl radical, a vinyl radical, a cyclopentyl radical, a cyclohexyl radical, a phenyl radical, and a diphenyl radical.

6. The hardener as claimed in claim 1, wherein radical R of radical $R^3$ of general formula (II) is an ethyl radical.

7. The hardener as claimed in claim 1, wherein the compound of the general formula (II) is at least one selected from a group comprising methyl-tris-(ethyl lactato)-silane, ethyl-tris-(ethyl lactato)-silane, and tetra-(ethyl lactato)-silane.

8. A method for curing a silicone rubber material comprising the steps of:
providing an organosilicone compound and a hardener as described in claim 1, and
mixing the organosilicone compound and hardener.

9. A composition, comprising the hardener as claimed in claim 1 and an organosilicone compound.

10. The composition as claimed in claim 9, wherein the organosilicone compound is an α,ω-dihydroxyl-terminated polyorganosiloxane compound.

11. The composition as claimed in claim 9, comprising from 40 to 90% by weight of the organosilicone compound and from 1 to 15% by weight of the hardener.

12. A method of forming a sealant, adhesive or coating material comprising the steps of:
providing an organosilicone compound and a hardener as described in claim 1, and
mixing the organosilicone compound and hardener, and exposing the mixture to water or humidity of the air at room temperature.

13. A method of preparing a hardener as claimed in claim 1, comprising:
   (I) reacting a compound of general formula $SiX_3R^2$ (III) with three equivalents of alkyl lactate (hydroxy-propionic acid alkyl ester), the alkyl radical of the alkyl lactate being selected from a group consisting of a methyl radical, an ethyl radical, a propyl radical and an isopropyl radical, and
   wherein radical $R^2$ is selected from at least one of a straight-chain or branched alkenyl or alkinyl radical, which each has at least two carbon atoms, and
   wherein radical X is selected from a group comprising an alkoxy radical, which has at least one carbon atom and a halogen atom; and
   (II) mixing the compound formed in step (I) with a compound having the general formula $Si(R^3)_n R^4_m$ (II), wherein
   n=1, 2, 3, or 4 and m=(4−n),
   radical $R^3$ is a 2-hydroxy-propionic acid alkyl ester radical of the general formula —$OCH(CH_3)COOR$,
   radical R is selected from a group consisting of a methyl radical, an ethyl radical, a propyl radical, and an isopropyl radical, and
   radical $R^4$ is at least one selected from a group comprising
   a straight-chain branched alkyl radical, which has at least one carbon atom,
   a straight-chain or branched alkenyl radical or alkinyl radical, which has at least two carbon atoms,
   a cycloalkyl radical, which has at least three carbon atoms, and
   an aryl radical, which has at least five carbon atoms.

14. The composition as claimed in claim 10, wherein the organosilicone compound is an α,ω-dihydroxyl-terminated polydialkylsiloxane.

15. The method as claimed in claim 13, wherein the halogen atom is a chlorine atom.

* * * * *

UNITED STATES PATENT AND TRADEMARK OFFICE
CERTIFICATE OF CORRECTION

Page 1 of 1

PATENT NO.        : 8,569,439 B2
APPLICATION NO.   : 12/673080
DATED             : October 29, 2013
INVENTOR(S)       : Ederer et al.

It is certified that error appears in the above-identified patent and that said Letters Patent is hereby corrected as shown below:

On the title page, item [73] Delete "Nitro-Chemie Aschau GmbH" and insert --Nitrochemie Aschau GmbH--.

Signed and Sealed this
Fourth Day of February, 2014

Michelle K. Lee
*Deputy Director of the United States Patent and Trademark Office*